(12) United States Patent
Kaufman et al.

(10) Patent No.: US 12,226,607 B2
(45) Date of Patent: Feb. 18, 2025

(54) RADIOPHARMACEUTICAL DELIVERY SYSTEM AND USE THEREOF FOR PATIENT INFUSION

(71) Applicant: Jubilant Draximage Inc., Montreal (CA)

(72) Inventors: James A. Kaufman, Montreal (CA); Dominic Siewko, Kirkland (CA); Indranil Nandi, Yardley, PA (US)

(73) Assignee: Jubilant Draximage Inc. (CA)

( * ) Notice: Subject to any disclaimer, the term of this patent is extended or adjusted under 35 U.S.C. 154(b) by 0 days.

(21) Appl. No.: 18/819,145

(22) Filed: Aug. 29, 2024

(65) Prior Publication Data

US 2024/0416031 A1    Dec. 19, 2024

Related U.S. Application Data

(63) Continuation of application No. 18/618,798, filed on Mar. 27, 2024, now Pat. No. 12,102,789.
(Continued)

(51) Int. Cl.
*A61M 5/142*    (2006.01)
*A61M 5/168*    (2006.01)
(Continued)

(52) U.S. Cl.
CPC ........ *A61M 5/142* (2013.01); *A61M 5/16831* (2013.01); *A61M 5/1785* (2013.01);
(Continued)

(58) Field of Classification Search
CPC .............. A61M 5/142; A61M 5/16831; A61M 5/1785; A61M 2005/14208; A61M 2005/16863; A61M 2202/0007; A61M 2202/049; A61M 2205/10; A61M 2205/18; A61M 2205/3327; A61M 2205/3331;
(Continued)

(56) References Cited

U.S. PATENT DOCUMENTS

2008/0177126 A1    7/2008    Tate et al.
2013/0123567 A1    5/2013    Agamaite et al.
(Continued)

*Primary Examiner* — Jason E Flick
(74) *Attorney, Agent, or Firm* — William D. Hare, Esq.; McNeely, Hare & War, LLP

(57) ABSTRACT

The invention is a theranostic delivery system or radiopharmaceutical drugs delivery system with movable workstation having handles. The workstation of theranostic delivery system or radiopharmaceutical drugs delivery system also has an on-board shielded disposal system for waste collection, which is operated by foot actuated system for locked and unlocked modes during the device journey. The theranostic delivery system or radiopharmaceutical drugs delivery system comprises a status light system that illuminates the working area to enable distance monitoring. Further, the delivery system includes a disposable secondary containment system that protects the core workstation from contamination, a configurable dose transporter and a disposable sealed fluid cartridge to withdraw custom volume from the vial or syringe. The delivery system includes a theranostic informatics management system, which contains a computer screen as a graphical user interface with a retractable rotating arm to receive the various patient infusion parameters.

20 Claims, 14 Drawing Sheets

Related U.S. Application Data

(60) Provisional application No. 63/492,628, filed on Mar. 28, 2023.

(51) Int. Cl.
  *A61M 5/178* (2006.01)
  *G16H 10/60* (2018.01)
  *G16H 40/63* (2018.01)

(52) U.S. Cl.
  CPC ............ *G16H 10/60* (2018.01); *G16H 40/63* (2018.01); *A61M 2005/14208* (2013.01); *A61M 2005/16863* (2013.01); *A61M 2202/0007* (2013.01); *A61M 2202/049* (2013.01); *A61M 2205/10* (2013.01); *A61M 2205/18* (2013.01); *A61M 2205/3327* (2013.01); *A61M 2205/3331* (2013.01); *A61M 2205/3379* (2013.01); *A61M 2205/502* (2013.01); *A61M 2205/584* (2013.01); *A61M 2205/6009* (2013.01)

(58) Field of Classification Search
  CPC .... A61M 2205/3379; A61M 2205/502; A61M 2205/584; A61M 2205/6009; A61M 5/14; A61M 5/168; A61M 2205/33; A61M 2205/50; A61M 2205/60; G16H 10/60; G16H 40/63; G16H 40/60; G16H 40/00
  See application file for complete search history.

(56) References Cited

U.S. PATENT DOCUMENTS

2020/0016284 A1    1/2020   Schimmoeller et al.
2022/0409793 A1*  12/2022   Marotta ................ A61M 1/159

* cited by examiner

RADIOPHARMACEUTICAL DELIVERY SYSTEM AND USE THEREOF FOR PATIENT INFUSION

TECHNICAL FIELD OF THE INVENTION

The present invention relates to a radiopharmaceutical infusion system. More particularly, the present invention relates to a theranostic or radiopharmaceutical drug delivery system which can perform patient infusion of radiopharmaceutical compositions in an outpatient care clinic and/or hospital by setting and pairing a novel syringe shield device, in combination with patient infusion pump device.

BACKGROUND OF THE INVENTION

Radiopharmaceuticals drugs are important for therapeutic and diagnostic use of various diseases. The safe and efficient use of these important and potentially dangerous radioisotopes having either short or long half-life are essential during their intended use by patient and/or healthcare providers. These radioisotopes play a vital role in the diagnosis and therapy of various diseases. Most of the widely accessible radiopharmaceuticals are generated by various known techniques. For example, Co-60 is used in the treatment of cancer, I-131 is used in the treatment of hyperthyroidism, C-14 is used in breath tests, Tc-99m, Rb-82 are used as tracers in myocardial perfusion imaging, Ga-68 is used for imaging of solid tumours, and Ac-225, Lu-177, and At-211 are used for therapeutic purposes. Due to the short half-lives of some radiopharmaceuticals, the entire imaging and administration procedure essentially needs to be completed within a short time period. Some radiopharmaceuticals are usually prepared at on-site facilities having a suitable driving distance from the patient site to prevent undue decay of the radiopharmaceutical prior to use. Additionally, these radioisotopes have undesirable radiation hazards side effects to the users or healthcare providers as well as to the patients. Therefore, safe handling techniques, including using shielded systems, are essential to avoid various undesirable health hazards.

Currently, Nuclear Medicine Technologists configure a non-radioactive chemotherapeutic/IV infusion peristaltic pump for infusion of theranostic radiopharmaceuticals to patients in hospitals. There is an unmet need in the technology of infusion systems for new generation theranostic/therapeutic radiopharmaceuticals that require a slow infusion (i.e. 1 ml/minute) whereas diagnostic infusions are of the "bolus" type, in addition to providing the safe/shielded delivery system and to minimize the undesirable health hazards to patients, users/healthcare providers and the environment from radiation exposure.

Currently, available infusion systems and methods have several disadvantages, such as no radiation shielding and lack of ability to flush, or wash, the drug syringe with saline to ensure adequate dose to the patient. Moreover, current methods do not incorporate a syringe; instead, they depend on extended spinal needles for piercing the rubber septum of a glass vial to withdraw the drug, which may lead to the introduction of air into the patient IV line, resulting in incomplete or inaccurate drug administration and the risk of air embolism to the patient. Further, not all infusion pumps can accommodate a 60cc syringe volume, which is the size required for infusion of some radiopharmaceuticals for therapy. There is an unmet need for an infusion system solution to carry all of the required specialty radiopharmaceutical procedure supplies to the patient, such as ion chamber, Geiger-Mueller counter, IV tubing, and radioactive waste. Also, there is guideline published in the USP General Chapter <825> on preparation, compounding, dispensing, and repackaging of Radiopharmaceuticals. According to the published compendium of drug information and standards, customers are prohibited from manipulating high activity drugs without a cleanroom and hospitals and pharmacies should comply with the guideline. The present invention will facilitate hospital and pharmacy compliance and safety by providing the quality controlled drugs in a shielded syringe for infusion to patients on a dose basis. More particularly, there is an unmet need to develop an advanced and efficient theranostic delivery system in combination with a radiation shielded syringe infusion pump which can provide increased radiation safety for the patient as well as for users/healthcare providers.

SUMMARY OF THE INVENTION

The present invention relates to a theranostic delivery system or radiopharmaceutical drugs delivery system which can perform patient infusion of radioactive therapeutic drugs in a hospital setting by pairing a novel syringe shield device in combination with patient infusion pump device.

An aspect of the present invention is to provide an ergonomic theranostic delivery system with a movable cart for transporting the therapeutic radiopharmaceutical dose to the patient infusion room in the hospital or clinic.

An aspect of the present invention is to provide patient specific theranostic dosing of different radiopharmaceutical theranostic drugs using an automated infusion system. However, it should be understood that the dose and administration of the radiopharmaceutical can be fully automated, semi-automated or manual.

An aspect of the present invention is to automate the infusion of radiopharmaceuticals for therapeutic purposes.

An aspect of the present invention is to facilitate the healthcare providers ability to monitor and protect their health from radiation hazards while treating the patient.

An aspect of the present invention is to provide localized radiation shielding to the syringe containing the radioactive drug.

An aspect of the present invention is to provide an infusion system which may deliver the radiopharmaceutical composition by using a process that is manual, automated, semi-automated, computer-controlled or any combination thereof.

An aspect of the present invention is that it allows the syringe to be "rinsed" with saline after infusion either automatically, semi-automatically, manually, and/or combinations thereof to ensure that the entire drug is injected.

An aspect of the present invention is to provide a "cart" with an accessory management system to allow the healthcare provider to keep all necessary supplies in ready-to-use conditions.

An aspect of the present invention is to provide a contamination management system comprising of a removal tray with an integral channel system to direct any fluid leak toward a collection pad or waste bin.

Yet another aspect of the present invention is to provide a theranostic informatics management system which controls the infusion parameter of the patient.

Another aspect of the present invention is a display to display different colours to show various states of operation of the device during use.

An aspect of the present invention is to provide a theranostic delivery system (100) that comprises:
i) an ergonomic movable cart with an integrated handle;
ii) a theranostic informatics system with a computer screen (19) as a graphical user interface (GUI);
iii) a shielded infusion pump; and
iv) a configurable dose transporter (6);

wherein the configurable dose transporter (6) comprises:
a) a separable radioactive dose transportation and containment module (13);
b) a shielding (18) optimized for different dose activities;
c) a radioactive dose in a standard syringe (8);
d) an one handed grip (12) to enable transfer of the radioactive dose from the dose transporter to an external dose calidrator;
e) an adapter (9) to convert a luer lock syringe type to pushfit connector; and
f) a sterile cap (11) with features that are an integral part of the workflow management.

An aspect of the present invention is to provide a theranostic delivery system (100) that comprises:
i) an ergonomic movable cart with an integrated handle;
ii) a shielding (18) that is optimized for different dose activities;
iii) a theranostic informatics system with a computer screen (19) as graphical user interface (GUI);
iv) a shielded infusion pump; and
v) a disposable sealed fluid cartridge (7);

wherein the disposable sealed fluid cartridge (7) comprises:
a) one or more selectable integrated flow channels (17);
b) one or more sealed no leak/no drip connections (10); and
c) one or more guide features and mechanical interlocks (16) for workflow management.

An aspect of the present invention is to provide a theranostic delivery system (100) that comprises:
i) an ergonomic movable cart with an integrated handle;
ii) a shielding (18) optimized for different dose activities;
iii) a theranostic informatics system with a computer screen (19) as graphical user interface (GUI);
iv) a shielded infusion pump; and
v) a workstation (3);

wherein the workstation (3) comprises:
a) a status light system (1) that illuminates the working area to enable long distance monitoring;
b) a disposable secondary containment system (2) that protects the core workstation from contamination (e.g., radioisotope, radiation);
c) an on-board, shielded disposal system (4); and
d) a foot actuated system (5) to enable locked and unlocked modes during the device journey, e.g., to lock and unlock wheels on the movable cart.

DETAILED DESCRIPTION OF THE INVENTION

Figure 1A:
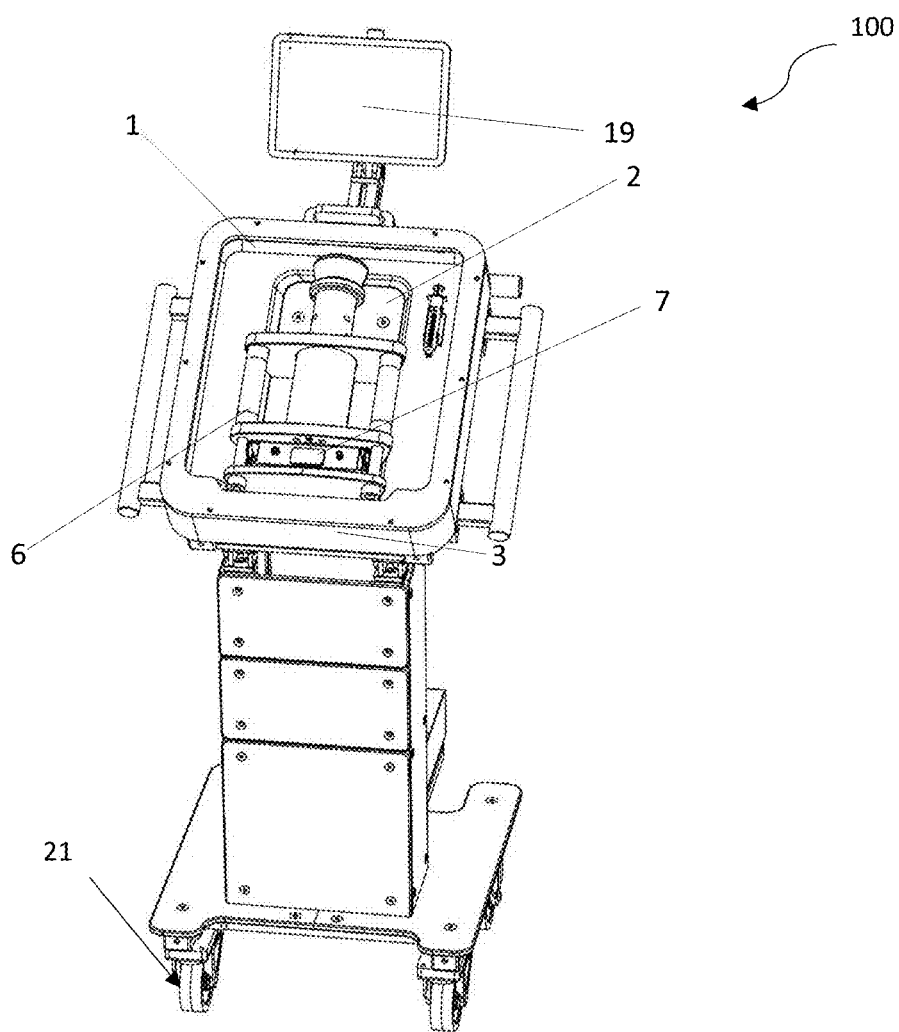
FIG. 1A and FIG. 1B show diagrams of a schematic representation of a theranostic delivery system or radiopharmaceutical drug delivery system.

The present invention can be more readily understood by reading the following detailed description of the invention and included embodiments.

The term "about" as used herein in the invention refers to a measurable value such as a parameter, an amount, a temporal duration, and the like, and is meant to encompass variations of and from the specified value, in particular variations of ±10% or less, preferably ±5% or less from the specified value, such variations are appropriate to perform in the disclosed invention. It is to be understood that the value to which the modifier "about" refers is itself also specifically, and preferably, disclosed.

As used in the specification of the present invention, the singular forms "a", "an", and "the" include plural references unless the context clearly dictates otherwise. Thus, for example, a reference to "a system" or "a device" or "a process" or "a composition" includes one or more systems, one or more device, one or more process or composition, with one or more steps or ingredients or elements of the type described herein and/or which will become apparent to those persons skilled in the art upon reading this disclosure and so forth.

As used herein, the term "imaging" refers to techniques and processes used to create images of various parts of the human body for diagnostic and treatment purposes within digital health. For example, imaging includes X-ray radiography, Fluoroscopy, Magnetic resonance imaging (MRI), Computed Tomography (CT), Medical Ultrasonography or Ultrasound Endoscopy Elastography, Tactile imaging, Thermography Medical photography, and nuclear medicine functional imaging techniques e.g. Positron Emission Tomography (PET), Dynamic Positron Emission Tomography and Single-photon Emission Computed Tomography (SPECT). Imaging is used to reveal internal structures of the body, and may be used to diagnose and treat disease.

As used herein, the term "SPECT" refers to a Single-Photon Emission Computed Tomography, a nuclear medicine tomographic imaging technique using gamma rays and providing true 3D information. This information is typically presented as cross-sectional slices through the patient, but can be freely reformatted or manipulated as required. The technique requires the delivery of a gamma-emitting radioisotope (a radionuclide) into the patient, normally through injection into the bloodstream. A marker radioisotope is generally attached to a specific ligand to create a radio-ligand and/or radiopharmaceutical, whose properties bind it to certain types of tissues. This allows the radiopharmaceutical to be carried and bound to a region of interest in the body, where a SPECT camera assesses the ligand concentration. The radioisotopes typically used in SPECT imaging are iodine-123 (I-123), indium-111 (In-111), technetium-99m (Tc-99m), xenon-133 (Xe-133), thallium-201 (Tl-201), krypton-87m (Kr-81m), and gallium-67 (Ga-67).

As used herein, the term "Positron Emission Tomography (PET)" refers to a functional imaging technique that uses radioactive substances known as radiotracers or radiopharmaceuticals to visualize and measure changes in metabolic processes, and in other physiological activities including blood flow, regional chemical composition, and absorption. Different radiotracers can used for various imaging purposes, depending on the target process within the body. The radioisotopes typically used in PET imaging are carbon-11 (C-11), nitrogen-13 (N-13), oxygen-15 (O-15), fluorine-18 (F-18), rubidium-82 (Rb-82), copper-64 (Cu-64), zirconium-89 (Zr-89), and gallium-68 (Ga-68).

As used herein, the terms "therapy" and "therapeutic use" refer to the attempt to cure, improve, mitigate, treat and/or prevent disease and/or other conditions in humans. The term "therapy" also refers to pharmacotherapy or pharmacological therapy, which refers to the treatment of disease through the application of medications (drugs). The term can be used to indicate treating or preventing development of a disease, as well as to alleviating the pain and symptoms of the particular condition. Nuclear medicine therapy can be given with the help of radioisotopes like alpha emitters actinium-225 (Ac-225), astatine-211 (At-211), etc. and beta emitters such as lutetium-177 (Lu-177), lead-212 (Pb-212), etc.

As used herein, the term "Computed Tomography (CT)" refers to computerized x-ray imaging in which a beam of x-rays aimed at a patient and rotated around the body, produces signals that are processed by the machine's computer to generate cross-sectional images of the body. These slices are tomographic images and contain more detailed information than conventional x-rays. Once the machine's computer collects a number of successive slices, they can be digitally "stacked" together to form a three-dimensional image of the patient that allows for easier identification and location of basic structures as well as possible tumors or abnormalities.

As used herein, the term "Magnetic Resonance Imaging (MRI)" is a non-invasive imaging technology that produces 3D detailed anatomical images, which is used for disease detection, diagnosis, and treatment monitoring. MRI is based on technology that excites and detects the change in the direction of the rotational axis of protons found in the water that makes up living tissues.

As used herein, the term "Hybrid Molecular Imaging" refers to the fusion of two or more imaging technologies into a single, new form of imaging. This form of imaging is synergistic, which is more powerful than the sum of its parts. Hybrid imaging denotes image acquisitions on systems that physically combine complementary imaging modalities for an improved diagnostic accuracy and confidence as well as for increased patient comfort. Hybrid imaging combines the strengths of two imaging modalities in one imaging session to more accurately diagnose and locate cancers while increasing patient comfort. These are generated by superimposing two images at two different spatial scales: the low-spatial scale is obtained by filtering one image with a low-pass filter; the high spatial scale is obtained by filtering a second image with a high-pass filter. Examples of hybrid imaging modalities include PET-CT, SPECT-CT and PET-MRI.

As used herein, the term "automated infusion system" or "semi-automated infusion system" refers to a system for generation and/or infusion of a radionuclide or radiotracer and administration into a subject. The automated infusion system and semi-automated infusion system include but are not limited to dose calidrator, computer, controller, display device, activity detector, cabinet, cart, waste management system, sensors, light display system, shielding assembly, alarms or alerts mechanism, tubing, source vial, diluent or eluent, pump, and valves and/or combinations thereof. The automated infusion system and semi-automated infusion system can be communicatively or electronically coupled to the imaging system.

As used herein, the term "diagnosis" refers to the process of identifying a disease, condition, or injury from its signs and symptoms. A health history, physical exam, and tests, such as blood tests, imaging, scanning, and biopsies can be used to help make a diagnosis. As used herein, the term "assessment" refers to a qualitative and/or quantitative assessment of the blood perfusion, solid tumours or any other diseases or abnormalities in a body part or region of interest (ROI).

As used herein, the term "ergonomic movable cart" refers to a wheeled cart that is ergonomic in design and easily movable or transportable.

As used herein, the term "infusion pump" refers to an infusion pump which can be shielded a radiation protection shield of radiation shielded material such as lead, tungsten or other radiation protection materials. The pump is a single drive pump system which is electronically controlled to draw interim volumes from various supply vessel types (saline, hot (e.g., radioisotope dose) to required volume and use that same system to infuse the patient with required control of flow rates and accuracy.

As used herein, the term "standard syringe" refers to a syringe with the standard volume. The syringes used herein were a patented and proprietary Jubilant shielded syringe according to U.S. Pat. No. 11,179,518 B2.

As used herein, the term "separable radioactive dose transportation and containment module" refers to a separable module wherein the syringe containing a radioactive dose is fitted and the module consists of (a) an one handed grip to enable transfer of the dose from the dose transporter to an external dose calidrator (b) an adapter to convert a syringe luer type to pushfit connector (c) a sterile cap with features that are an integral part of the workflow management. The sterile cap is used to protect the syringe from leakage and also protect from radiation emitted from the radiopharmaceutical drugs containing in the syringe.

As used herein, the term "dose calidrator" refers to a device which is used in nuclear medicine to determine the exact activity of a radioactive dose to be administered to the patient.

As used herein, the term "luer lock syringe" refers to a syringe that enables a needle to be twisted onto the tip and be locked into place, providing a secure connection and preventing accidental removal of the needle as well as accidental injection of contents.

As used herein, the term "medical fluid" refers to a radiopharmaceutical drug for patient infusion.

As used herein, the term "infusion parameter" refers to one or more of infusion rate, infusion mode, desire dose, desired activity and/or any patient infusion related data.

As used herein, the term "contamination management system" refers to a removable tray with integral channel system to direct any fluid leaks towards a collection pad or waste bin.

As used herein, the term "radioactive-dose" refers to the dose of a radiopharmaceutical composition required to perform imaging in a subject, wherein the radiopharmaceutical composition comprises an active radioisotope used for imaging and therapy. The dose of a radionuclide to be administered to the subject ranges from 0.27 uCi to 1000 mCi.

As used herein, the term "accessory management system" refers to a cabinet or box for storage purposes.

As used herein, the term "graphical user interface (GUI)" refers to an interface through which a user interacts with devices such as computers. Here, a computer screen is functioning as a GUI.

As used herein, the term "shielding" refers to a shielding for different size dose activities. Here the different dose activities refer to the different volume of the syringe, which consist of the hot dose (i.e. radiopharmaceutical drug). The volume of the syringe can be 10cc, 20cc, 30cc, 60cc syringe and the volume of the vial is up to 30cc in volume. The dose shielding is used to shield the syringe of different size and diameter, wherein the shielding (18) system is suitable for a variety of sizes of the syringe being inserted or connected. The shielding may selected from a variety of suitable materials including lead and tungsten. In one configuration the shielding is fixed at 0.25 inch thick tungsten, which will be sufficient to shield of any volume or type of therapeutic radiation. The shield defines an internal cavity that is suitable for receiving and holding either a syringe or vial with the fluid cartridge. Although a single shield can be used for all applications, if desired shields of different sizes are included within the scope of the invention.

As used herein, the term "configurable dose transporter" refer to a "Caddy" that allows for safe transport of the hot dose between the hot lab and the infusion site. The configurable dose transporter comprises; a separable radioactive dose transportation and containment module (13); a shielding (18) optimized for different dose activities; a radioactive dose in a standard syringe (8); an one handed grip (12) to enable transfer of the radioactive dose from the dose transporter to an external dose calidrator.

As used herein, the term "shielded disposal system" refers to a shield waste management system with pedal actuated waste bin to avoid using hands to open a lid of the waste bin, a space for the disposal bin and/or a waste bin.

As used herein, the term "Theranostic informatics system" refers to programmable software to control the operation of the delivery system.

As used herein, the term "pushfit connector" refers to a type of easily removed compression fitting or quick connect fitting that allows an equipment to be attached, nominally without the use of tools.

As used herein, the term "PET" is Positron emission tomography (PET), which is one type of diagnostic imaging. PET utilizes doses of a radiopharmaceutical, for example, generated by elution within a radioisotope generator, that are injected, or infused into a patient. The infused dose of radiopharmaceutical is absorbed by cells of a target organ of the patient, and emits radiation, which is detected by a PET scanner, in order to generate an image of the organ.

As used herein, the term "Theranostic delivery system" refers to the radiopharmaceutical drug delivery movable cart with shielded syringe and infusion pump device. The term "theranostic delivery system" and "radiopharmaceutical drugs delivery system" refer to a same drug infusion system with the same functionality.

As used herein, the term "system error" refers to an error in the infusion system such as wrong eluant, undesirable profile such as wrong infusion rate, wrong infusion mode, undesired dose, and undesired activity.

As used herein, the term "controller" or "control system" refers to a computer or a part thereof programmed to perform certain calculations, execute instructions, and control various activities of an infusion system based on user input or automatically.

As used herein, the term "coded port" refers to two ports on the fluid cartridge, i.e., patient port and saline/cold port, one for saline in and one for drug out. They are of different configuration types so the user will not confuse the two and create a patient error.

As used herein, the term "adapter" refers to a connector which is used to connect the syringe or vial with the disposable sealed cartridge via compression fitting. The adapter can be tagged, which means that the adapter is tagged with RFID, barcode, QR code and other such tags.

In an embodiment of the present invention, a theranostic delivery system (100) comprises:
  i) an ergonomic movable cart with integrated handle;
  ii) a theranostic informatics system with a computer screen (19) as a graphical user interface (GUI);
  iii) a shielded infusion pump; and
  iv) a configurable dose transporter (6);
wherein the configurable dose transporter (6) comprises:
  a) a separable radioactive dose transportation and containment module (13);
  b) a shielding (18) that is optimized for different dose activities;
  c) a radioactive dose in a standard syringe (8);
  d) an one handed grip (12) to enable transfer of the radioactive dose from the dose transporter to an external dose calidrator;
  e) an adapter (9) to convert a luer lock syringe type to pushfit connector; and
  f) a sterile cap (11) with features that are an integral part of the workflow management.

In an embodiment of the present invention, a theranostic delivery system (100) comprises:
  i) an ergonomic movable cart with integrated handle;
  ii) a shielding (18) that is optimized for different dose activities;
  iii) a theranostic informatic system with a computer screen (19) as graphical user interface;
  iv) a shielded infusion pump; and
  v) a disposable sealed fluid cartridge (7);

wherein the disposable sealed fluid cartridge (7) comprises:
a) one or more selectable integrated flow channels (17);
b) one or more sealed no leak/no drip connections (10); and
c) one or more guide features and mechanical interlocks (16) for workflow management.

In an embodiment of the present invention, a theranostic delivery system (100) comprises:
i) an ergonomic movable cart with an integrated handle;
ii) a shield (18) that is optimized for different dose activities;
iii) a theranostic informatics system with a computer screen (19) as a graphical user interface;
iv) a shielded infusion pump; and
v) a workstation (3);
wherein the workstation (3) comprises:
a) a status light system (1) that illuminates the working area to enable distance or long distance monitoring;
b) a disposable secondary containment system (2) that protects the core workstation from contamination;
c) an on-board shielded disposal system (4); and
d) a foot actuated system (5) to enable locked and unlocked modes during the device journey.

An embodiment of the present invention includes the delivery system, wherein the computer screen (19) is foldable and has a retractable rotating arm (20).

An embodiment of the present invention includes the delivery system, wherein the syringe (8) can be of different size and/or volume. Furthermore, the delivery system also supports the manufacturer's vial. In one implementation, the delivery system has the ability to infuse a 10cc, 20cc, 30cc, 60cc syringe and a vial of up to 30cc in volume.

An embodiment of the present invention includes the delivery system and further comprises a control system to control the process of infusion of medical fluid.

An embodiment of the present invention includes the delivery system, wherein the status light system (1) is controlled by the control system.

An embodiment of the present invention includes the delivery system and further comprises a theranostic informatics management system which controls the infusion parameters for the patient.

An embodiment of the present invention includes the delivery system and further comprises a contamination management system. The contamination management system comprises a removal tray with integral channel system to direct any fluid leak toward a collection pad or waste bin.

An embodiment of the present invention includes the delivery system, wherein the delivery system further comprises an accessory management.

An embodiment of the present invention includes the delivery system with the accessory management and the accessory management comprises storage for infusion supplies such as chux, gloves, and other articles as needed.

An embodiment of the present invention includes the delivery system to provide patient specific theranostic dosing of different radiopharmaceutical theranostic drugs using the automated infusion system.

An embodiment of the present invention includes the delivery system, wherein the graphical user interface (GUI) is used to receive the infusion parameters like infusion rate, infusion mode, desire dose, desired activity and/or any patient infusion related data. The patient specific dosing is based on the patient profile data, which includes patient weight, sex, age, or patient physical and health history data.

In an embodiment the present invention includes the delivery system (100), wherein the delivery system supports drug-specific infusion parameters, which means that for different radiopharmaceutical drugs the infusion parameter may be different. This feature is supported by using the custom software with drug-specific infusion parameters.

In an embodiment of the present invention, a radiopharmaceutical drugs delivery system (100) comprises:
(i) an ergonomic movable cart with an integrated handle;
(ii) an informatics system with a computer screen (19) as a graphical user interface (GUI);
(iii) a shielded infusion pump; and
(iv) a configurable dose transporter (6);
wherein the configurable dose transporter (6) comprises:
a) a separable radioactive dose transportation and containment module (13);
b) a shielding (18) that is optimized for different radionuclide types, quantities and volume;
c) a radioactive dose in a syringe (8) or vial (26); and
d) a disposable sealed fluid cartridge (7) connected to a syringe (8) or vial (26) via compression fitting.

In an embodiment of the present invention, a radiopharmaceutical drug delivery system (100) comprises:
(i) an ergonomic movable cart with an integrated handle;
(ii) an informatics system with a computer screen (19) as a graphical user interface (GUI);
(iii) a shielded infusion pump;
(iv) a status light system (1) that illuminates the working area to enable distance or long distance monitoring; and
(iv) a configurable dose transporter (6);
wherein the configurable dose transporter (6) comprises:
a) a separable radioactive dose transportation and containment module (13);
b) a shielding (18) that is optimized for different radionuclide types, quantities and amounts;
c) a radioactive dose in a syringe (8) or vial (26); and
d) a disposable, sealed fluid cartridge (7) connected to a syringe (8) or vial (26) via a compression fitting;
wherein the disposable sealed fluid cartridge permits a healthcare profession to withdraw a custom volume from the vial or syringe.

An embodiment of the present invention includes the delivery system with the syringe, wherein the syringe (8) can be one of multiple different standard sizes.

An embodiment of the present invention includes the delivery system, wherein the shielding (18) system is configured to be suitably used with a large range and variety of sizes of the syringe (8) being inserted or connected.

An embodiment of the present invention includes the delivery system, wherein the computer screen (19) as a graphical user interface (GUI) mounted to a retractable rotating arm.

An embodiment of the present invention includes the delivery system, wherein the fluid cartridge permits withdrawing a custom volume based on patient weight, sex, age, other physical parameter or health history data.

An embodiment of the present invention includes the delivery system, wherein the delivery system supports the drug specific infusion parameter.

An embodiment of the present invention includes the delivery system, wherein the separable radioactive dose transportation and containment module (13) is shielded with a lead glass viewing area (29).

An embodiment of the present invention includes the delivery system, wherein the fluid cartridge includes a coded port to eliminate errors in patient line or saline line.

An embodiment of the present invention includes the delivery system, wherein the system monitors and tracks one or more of: total volume in syringes, total volume administered in real-time, total volume from an IV bag, total volume infused into patient.

An embodiment of the present invention includes the delivery system and further comprises a control system to control the process of infusion of a medical fluid.

An embodiment of the present invention includes the delivery system, wherein the controller is configured to halt the infusion process upon detecting a system error.

An embodiment of the present invention includes the delivery system, wherein the status light system (1) indicates the different states of the device (e.g., administration, administration completed) with various colours.

An embodiment of the present invention includes the delivery system, wherein the status light system (1) is controlled by the control system.

An embodiment of the present invention includes the delivery system, wherein the system has an audible alarm feature to alert the user to one or more of fluid occlusions, pump failure or any deviation from the programmed volume and/or expected sequence of events in real-time An embodiment of the present invention includes the delivery system, wherein the pump protects the patient from an air infusion causing an air embolism and includes an alarm signal for air detection in real-time.

In an embodiment of the present invention a radiopharmaceutical drugs delivery system comprises;
a configurable dose transporter (6); a separable radioactive dose transportation and containment module (13); a shielding (18); a disposable sealed fluid cartridge (7); and a syringe (8) or vial (26);
wherein the disposable sealed fluid cartridge (7) comprises:
(i) one or more selectable integrated flow channels (17);
(ii) an adapter (9) to fit the syringe (8) or vial;
(iii) a coded patient port and a saline port; and
(iv) one or more pressure sensors (27, 28);
wherein the disposable sealed fluid cartridge is allowed to withdraw a custom volume from the vial (26) or syringe (8).

An embodiment of the present invention includes the delivery system (100), wherein the adapter (9) of a disposable sealed fluid cartridge (7) is connected to a syringe (8) or vial (26) via compression fitting to reduce leaking connections.

An embodiment of the present invention includes the delivery system (100), wherein the fluid cartridge withdrawn custom volume is based on one or more of patient weight, sex, age, health history data and/or other physical parameter.

An embodiment of the present invention includes the delivery system, wherein the controller is configured to halt the infusion process due to a system error.

An embodiment of the present invention includes the delivery system, which is programmed with software that is capable of being remotely updated to add new functionality and drug compatibility. The software also has security features to ensure the correct patient and/or the correct dose.

An embodiment of the present invention includes the delivery system, which includes software security programmed to prevent the unauthorized access and may have software firewall capability to prevent hackers and unauthorized remote access to patient data.

An embodiment of the present invention includes the delivery system with an infusion pump in which the infusion pump is indicated for intravenous and intra-arterial delivery of theranostic radiopharmaceutical agents at controlled infusion rates or as a bolus injection combined with a commercially available normal 0.9% saline supply. The infusion pump will only be compatible with various unit dose or multi-dose syringes or vials.

An embodiment of the present invention includes the delivery system, wherein the system has an audible alarm feature to alert the user to fluid occlusions, pump failure or any deviation from the programmed volume and/or expected sequence of events in real-time.

An embodiment of the present invention includes the delivery system, wherein the pump protects the patient from an air infusion causing air embolism and includes an alarm signal for air detection that is activated in real-time. The pump shall have protection such that after an air detection with accompanying alarm signal, it is not possible to continue liquid drug delivery by a single action. This advantageously prevents the operator from easily overriding a safety warning and potentially endangering a patient.

An embodiment of the present invention includes the delivery system, which includes a pressure sensor to monitor fluid occlusion in real time.

FIG. 1A, FIG. 1B, FIG. 1C and FIG. 1D illustrate the configuration of a theranostic delivery system or radiopharmaceutical drugs delivery system (100). The system (100) includes a mobile or movable ergonomic workstation (3) having handles on the side or back to move the cart via wheels (21). The workstation (3) of the theranostic delivery system (100) also includes an on-board shielded disposal system (4) (see FIG. 1B) for waste collection. The shielded disposal system (4) is operated by a foot actuated system (5) that enables locked and unlocked modes of the wheels during transport of the device (100). The theranostic delivery system or radiopharmaceutical drugs delivery system (100) also includes a foldable computer screen (19) mounted to a retractable rotating arm (20) and a status light system (1) that illuminates the working area, which enable the operator to monitor status of the system from a distance within the working area. The primary objective of distance monitoring is to keep the provider a distance from the radioactive patient to ensure low exposure. For example, if a healthcare provider is using the delivery system (100) to provide a radiopharmaceutical dose to a patient, and the provider needs to walk out of the room and across the hall, the provider will be able to easily glance at the delivery system and see that the status light system (1) is, for example green or blue, indicating operation is proceeding properly. Conversely, if the provider sees the status light system (1) go from green to orange or red, the provider will know to return quickly to investigate the change in status. The theranostic delivery system (100) in FIG. 1B also includes a disposable secondary containment system (2) that protects the core workstation from contamination. The theranostic system (100) in FIG. 1C includes a configurable dose transporter (6) with a disposable sealed fluid cartridge (7). The theranostic delivery system or radiopharmaceutical drug delivery system (100) also includes a storage tray (22) and storage space (23) to store the medical equipment and other necessary items for radiopharmacy administration.

Figure 2:
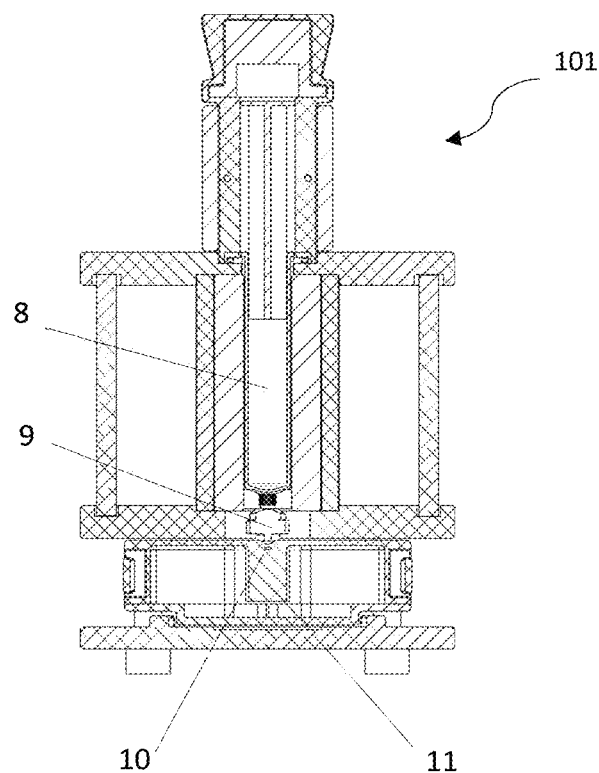
FIG. 2 shows a diagram of a schematic representation of a shielded syringe system.

FIG. 2 shows a cross-sectional view of a schematic representation of a shielded syringe system (101). The radioactive dose standard syringe (8) is shielded by shielding materials, i.e., lead, steel, tungsten or combinations of shielding materials. The shielding materials are configured in the shape of a cylinder (14) that is positioned around the syringe (8). The theranostic delivery system (100) also includes an adapter (9) to convert a syringe luer type to pushfit connector with sterile cap (11) having a no leak/no drip connection (10).

Figure 1B:
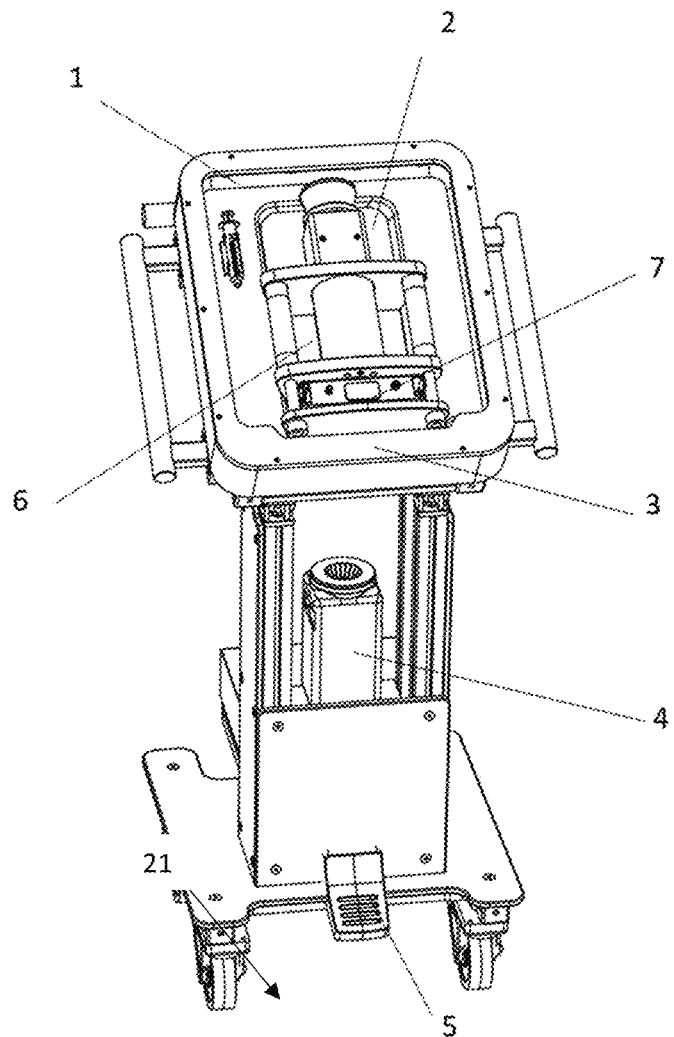
Figure 1C:
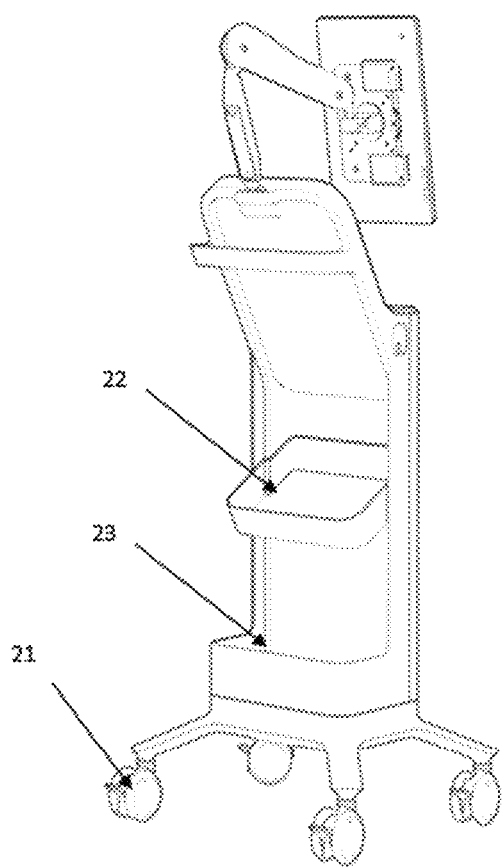
FIG. 1C and FIG. 1D represent the back and front views, respectively, of the theranostic delivery system or radiopharmaceutical drug delivery system.
Figure 1D:
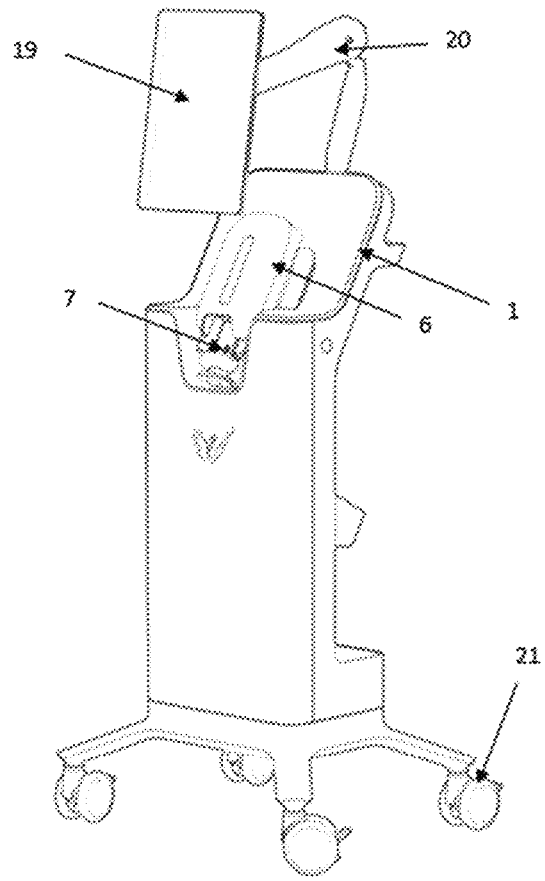
Figure 3:
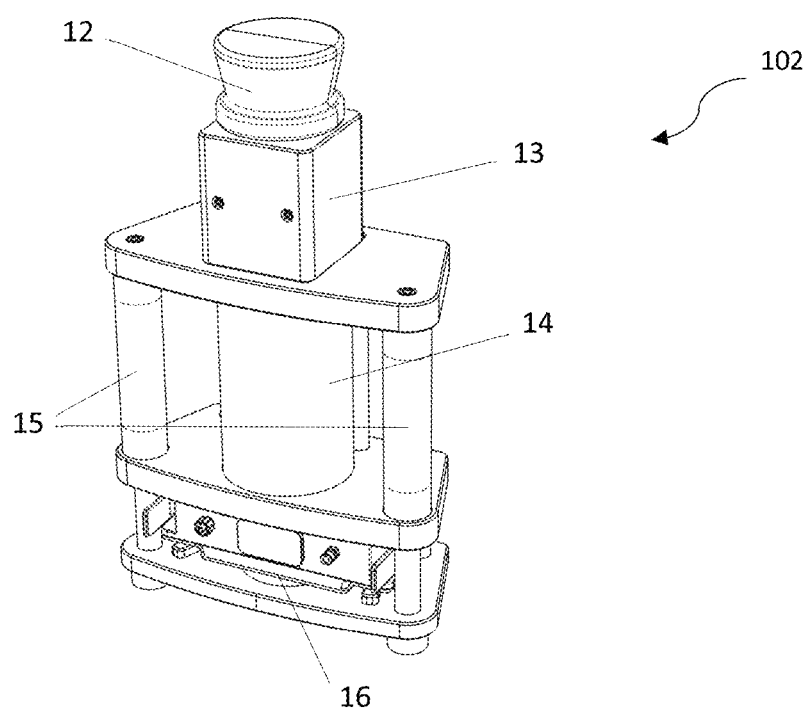
FIG. 3 shows a diagram of a schematic representation of a configurable dose transporter.

FIG. 3 shows a diagram (102) of a schematic representation of a configurable dose transporter (6) (as shown in FIG. 1A) having integrated handles (15) to enable two hands transfer from a shipping bag to radioactive dose prepared to be installed in workstation (3) for infusion (as shown in FIGS. 1A and 1B) and having one handed grip (12) to enable transfer of the dose from dose transporter (6) (as shown in FIGS. 1A and 1B) to an external dose calidrator for the measurement of the activity of the radiopharmaceutical drugs before infusion. The dose transporter (6) (as shown in FIGS. 1A and 1B) includes onboard shielding (14) with protection throughout the workflows in shipping, preparation and transport. The configurable dose transporter (6) (as shown in FIGS. 1A and 1B) further includes guide features and mechanical interlocks (16) for workflow management and a separable radioactive dose module (13). The separable radioactive dose module consist of a syringe with the hot dose to be infused into a patient.

Figure 4:
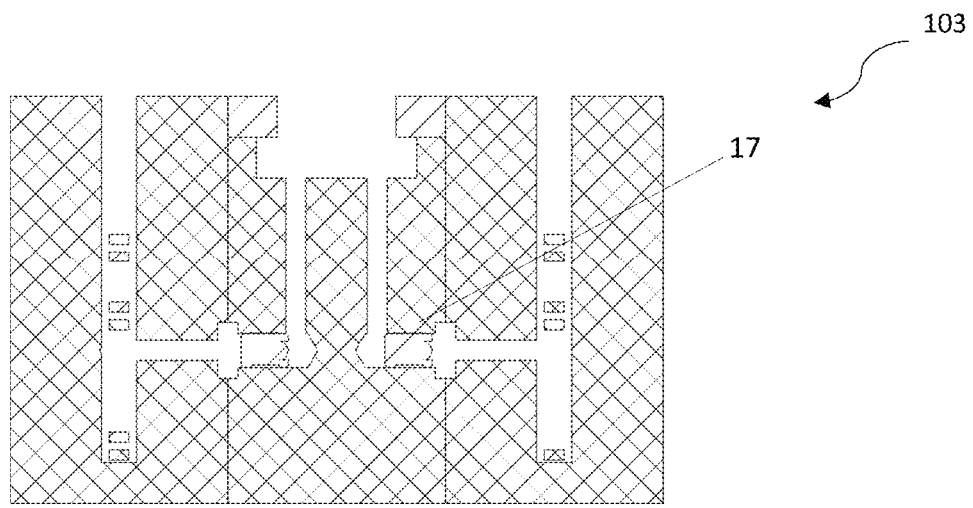
FIG. 4 shows a diagram of a disposable sealed fluid cartridge that contains selectable integrated flow channels, e.g., to connect the radioisotope dose source and the saline source to the infusion pump and the channel that is connected to a patient line for infusion of the desired radioisotope dose to a patient. The flow channels allow for bi-directional flow of fluid, for drug delivery to a patient and backwash with saline to "rinse" the cavity of any remaining radiopharmaceutical drug.

FIG. 4 shows a diagram (103) of a disposable sealed fluid cartridge (7) (as shown in FIG. 1A) of theranostic delivery system or radiopharmaceutical drugs delivery system (100) that contains one or more selectable integrated flow channels (17). The flow channel refers to the channel that is used to connect the hot dose source, saline source to the infusion pump and then that channel back connected to a patient line for infusion of the accurate dose to patient.

Figure 5:
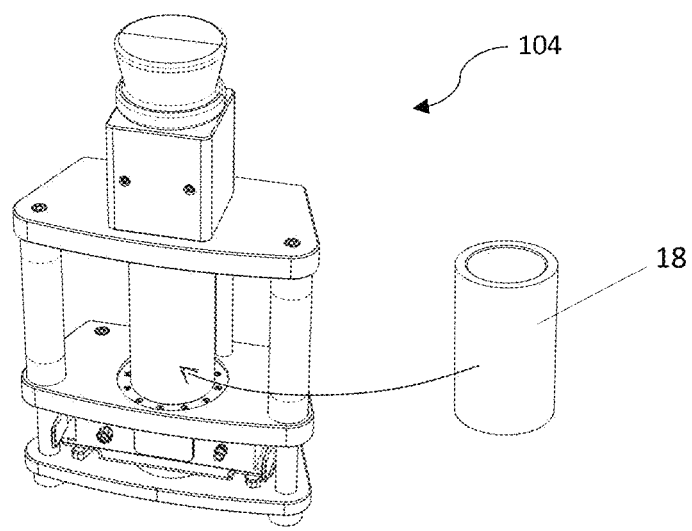
FIG. 5 shows a diagram of a shielding that is optimized for different dose activities.

FIG. 5 shows a diagram (104) of the shielding (18) of theranostic delivery system or radiopharmaceutical drugs delivery system (100) that is optimized for different dose activities. Here the different dose activities refer to the different volume of syringe, which consist of the hot dose (i.e., radiopharmaceutical drugs). The volume of the syringe can be 10cc, 20cc, 30cc, 60cc syringe and a volume of the vial is up to 30cc in volume. The dose shielding is used to shield the syringe of different size and diameter, wherein the shielding (18) system is able to be used with different sizes of the syringe being inserted or connected.

Figure 6:
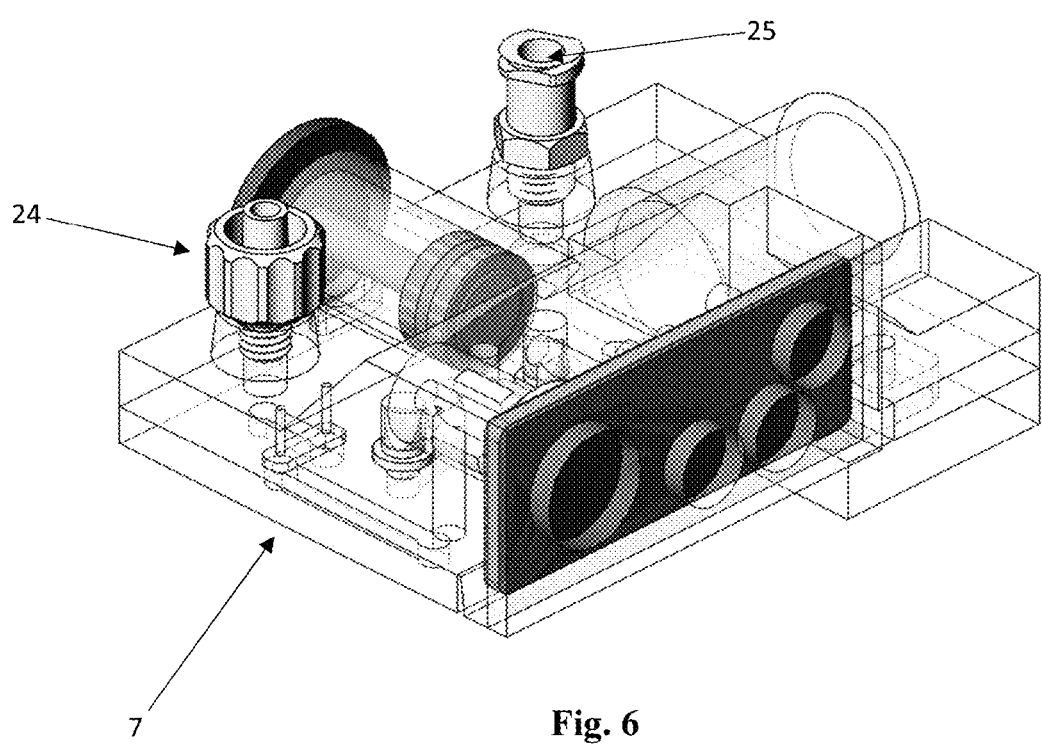
FIG. 6 shows a diagram of a disposable sealed fluid cartridge (7), which allows the healthcare provider to withdraw a custom volume from a vial or syringe.

FIG. 6 shows a diagram of disposable sealed fluid cartridge (7) with patient port (24) and saline/cold port (25) having a cavity that will allow custom volumes to be withdrawn from a vial or syringe. The cartridge includes a pump system to draw the required volumes from various supply vessel types (saline, hot dose) to an interim volume (i.e., "Transfer") and use that same system to infuse the patient with the radiopharmaceutical with the required control of flow rates, accuracy, etc.

Figure 7:
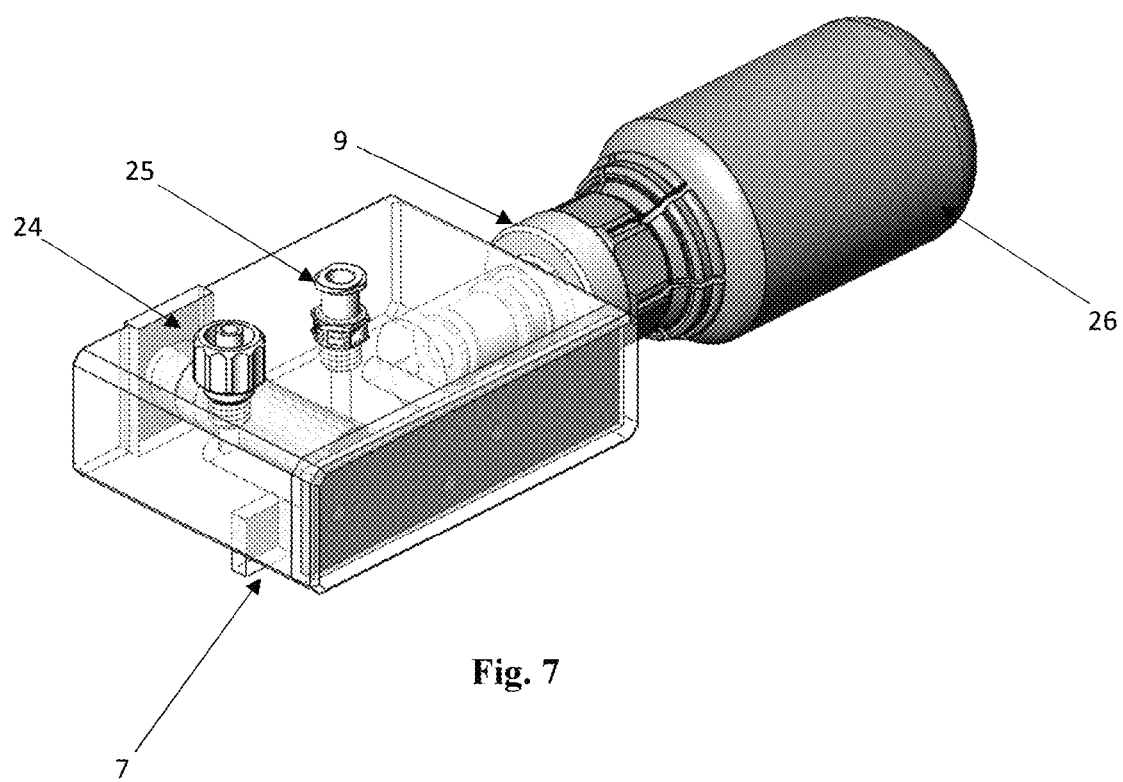
FIG. 7 shows a diagram of a disposable sealed fluid cartridge (7) in a connection with a vial (26) via a compression fitting.
Figure 8:
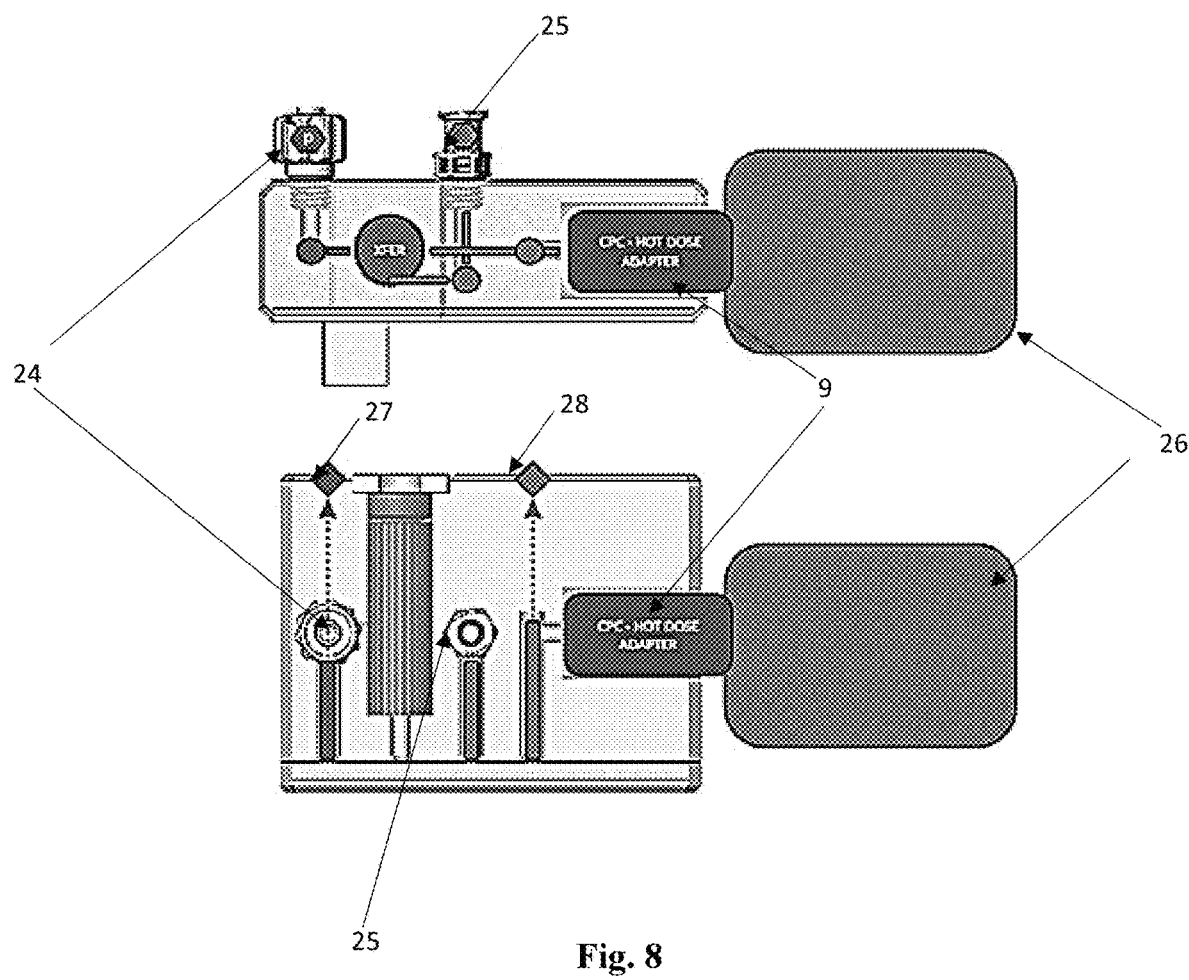
FIG. 8 shows a diagram of a disposable sealed fluid cartridge (7) with a dose adapter (9) in a connection with the vial (26) via compression fitting with coded port to eliminate errors in patient/saline lines.

FIG. 7 illustrates a disposable sealed fluid cartridge (7) in a connection with the vial (26) via a compression fitting with the help of adapter (9), which optionally may be tagged. FIG. 8 illustrates the connection of the disposable sealed fluid cartridge (7) with adapter (9) in connection with the vial (26) via compression fitting with coded port to eliminate errors in patient/saline lines. The disposable fluid cartridge (7) consists of one or more automated ON/OFF check valves which are connected with the hot dose source channel and the saline source channel to withdraw the drug and saline from the source vessel. Further, the hot dose channel and saline channel are connected with the infusion pump to infuse the required dose to the patient from the patient line.

Figure 9:
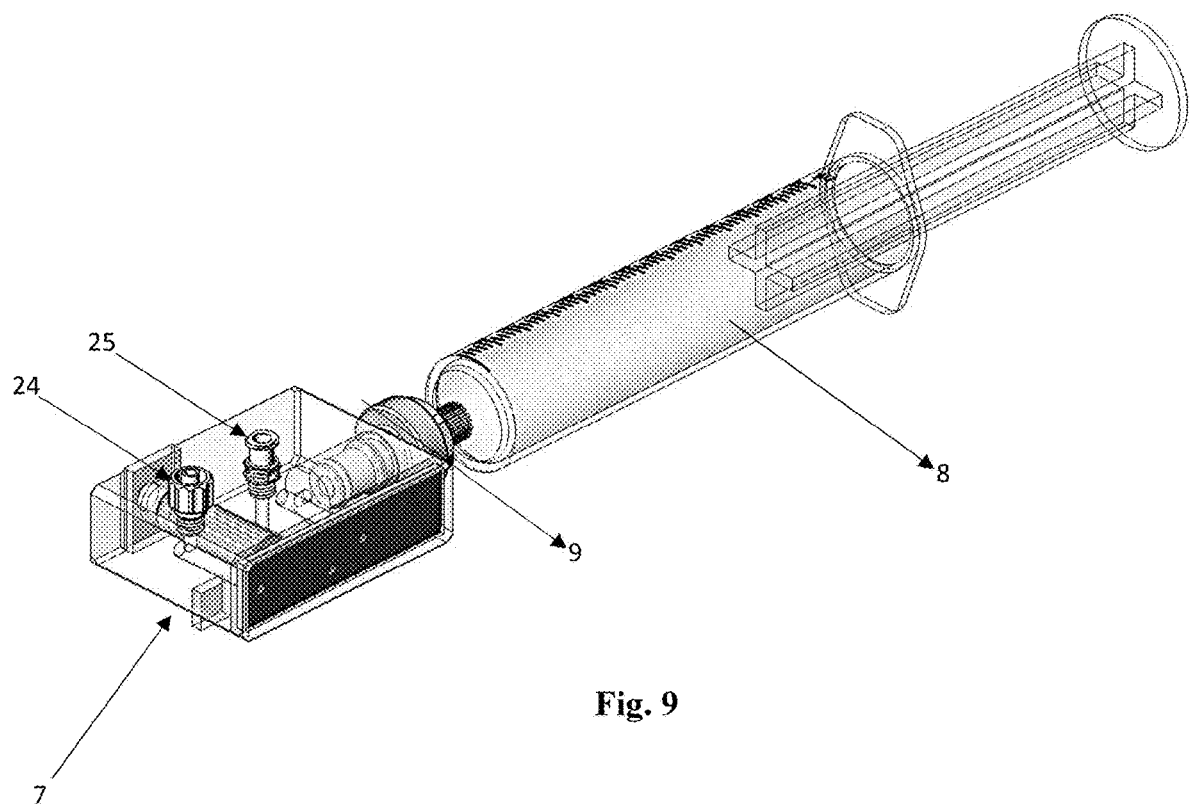
FIG. 9 shows a diagram of a disposable sealed fluid cartridge (7) connected to a syringe via a compression fitting to reduce leaking connections.
Figure 10:
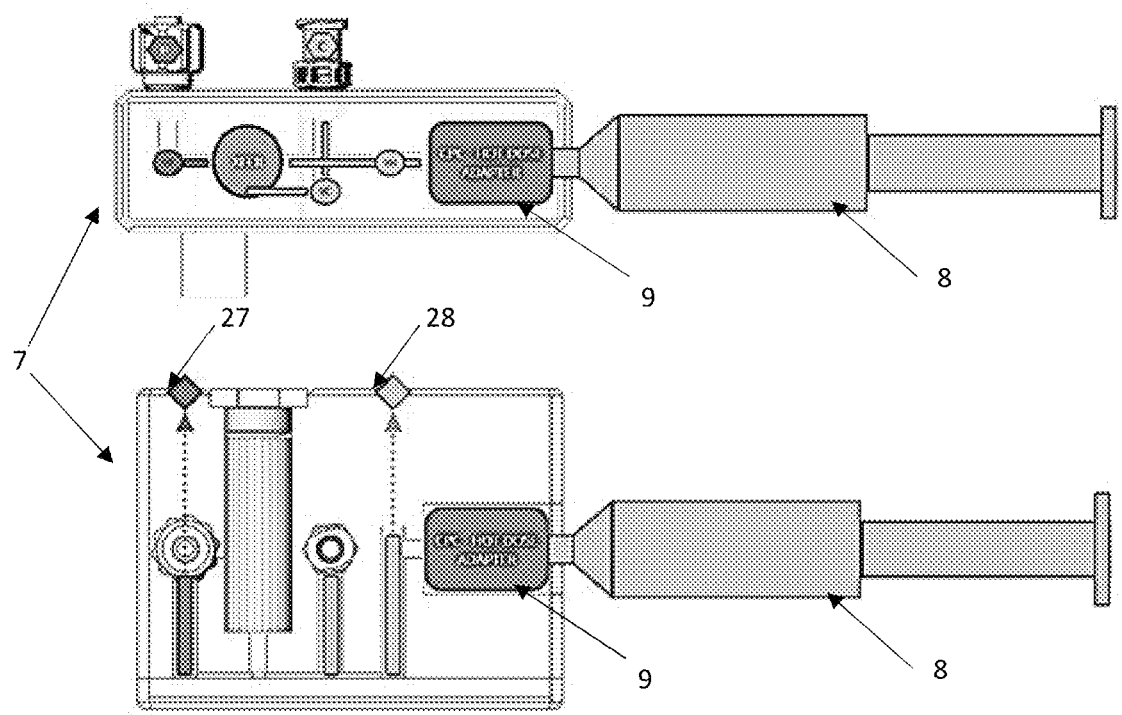
FIG. 10 shows a diagram of a disposable sealed fluid cartridge (7) with an adapter (9) in a connection with the syringe (8) via a compression fitting with a coded port to eliminate errors in patient/saline lines.

FIG. 9 illustrates a disposable sealed fluid cartridge (7) connected to syringe (8) via a compression fitting with the help of an adapter (9) to reduce leaking connections. FIG. 10 illustrates the connection of the disposable sealed fluid cartridge (7) with the adapter (9) in a connection with the syringe (8) via compression fitting with coded port to eliminate errors in patient/saline lines.

Additionally, the disposable sealed fluid cartridge (7) consists of two pressure sensors that are patient line pressure sensor (27) to measure the pressure in patient line and hot dose pressure sensor (28) to detect the pressure of dose from syringe (8) or vial (26) (as shown in FIGS. 8 and 10).

Figure 11:
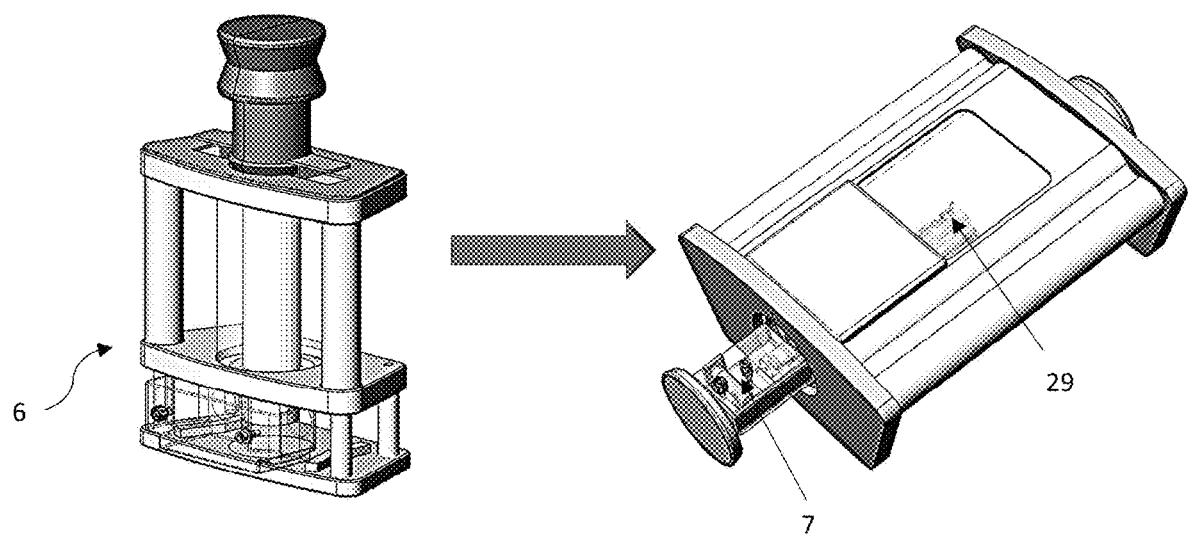
FIG. 11 shows a diagram of a configurable dose transporter (6) that is caddy connected in line with custom disposable sealed fluid cartridge (7) shielded with a viewing window (29) of lead glass.

FIG. 11 illustrates a configurable dose transporter (6) that is caddy connected in line with a custom disposable sealed fluid cartridge (7) shielded with a viewing window (29) of lead glass.

Figure 12:
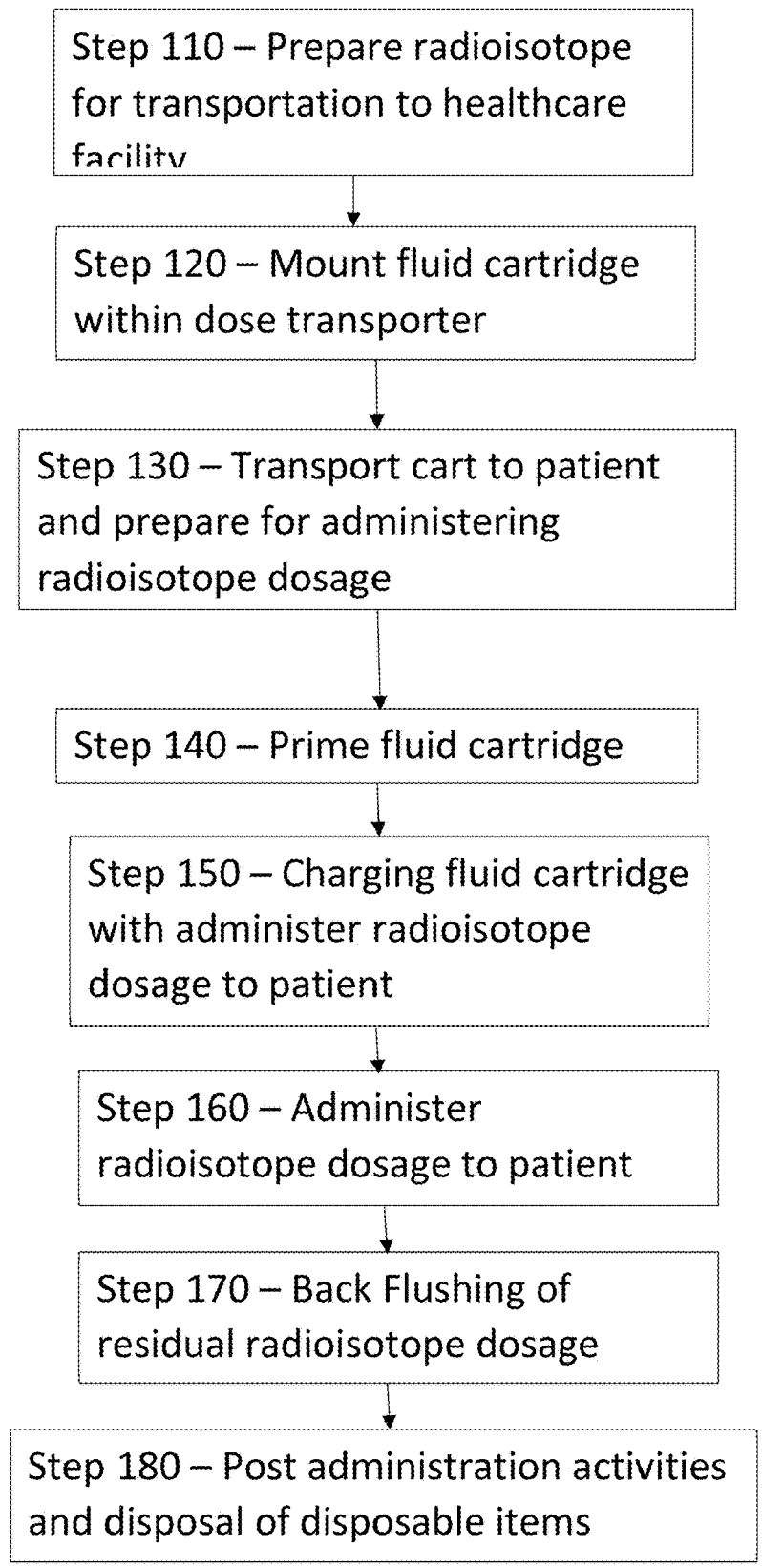
FIG. 12 is a flow chart showing use of the system to prepare and administer a radioisotope dose to a patient in a hospital or outpatient clinic.

FIG. 12 is a flowchart showing operation of the delivery system 100. In a first step 110, a radioisotope dose is prepared and placed in a container suitable for the radioisotope. The container may be the syringe (8) or vial (26) described above. The syringe or vial then is placed in the dose transporter (6) by grasping the upper grip (12) and pulling out the containment module (13) from the dose transporter. The syringe or vial is inserted into an opening in the containment module, which then is placed back into the dose transporter. Because of the shielding (14) component of the transporter, the healthcare provider is protected from the radioactivity of the radioisotope within the syringe or vial. Typically this dose is prepared elsewhere and transported to a radiopharmacy or hospital in a carrying enclosure, such as a bag, box or other container. The shielding component (14) protects those coming into contact with the dose transporter from exposure to radioactivity while the radioisotope is being transported to the radiopharmacy or hospital.

In a second step 120, the radioisotope dose is received in the carrying enclosure at a radiopharmacy or hospital lab and prepared for injecting into a patient. The radioisotope dose is within the dose transporter (6) when the carrying enclosure is received at the radiopharmacy or hospital. The healthcare provider removes the dose transporter from the carrying enclosure, places it on a surface such as a counter in a laboratory, and removes the containment module (13) from the dose transporter. Because this can expose the healthcare provider to radiation, the provider puts the containment module (13) into a shielded container, such as a shielded tube, for temporary storage during cartridge preparation. The shielded tube may be round, square or any convenient configuration suitable for holding and containing the module (13). With the containment module removed from the transporter (6), the provider next removes the sterile cap positioned at the lower side of the dose transporter.

With the sterile cap removed from the dose transporter, a volume with the transporter is exposed. The volume is defined on a lower surface by a first plate and an upper surface by a second plate. One or both of the first and second plates may include guides or grooves for receiving the fluid cartridge (7). The guide or grooves are configured to mate with the bottom, top and/or side surfaces of the fluid cartridge so that the cartridge can only be received within the volume in a single orientation. This safety feature prevents incorrect insertion of the fluid cartridge. In one implementation, the plates have guides and/or grooves and interlocks. When the fluid cartridge is positioned against the guides or grooves, the interlocks may be used to retain the cartridge in place. The interlocks may be configured to have a first part on the guide, groove or plate and a second part on the fluid cartridge. In this manner a snapping noise and/or tactile sensation noticeable to the provider may be experienced when the cartridge is properly oriented and in position.

The provider inserts the cartridge into the volume and advances until the proper placement is achieved, e.g., by experiencing the snapping noise and/or tactile sensation. The provider then grasps the upper grip (12) on the containment module (13), removes the module from the shielded container and inserts the opposite or lower end of the module into the opening at the top surface of the uppermost plate of the dose transporter. Generally, this uppermost plate is different from the upper plate defining the volume for receiving the fluid cartridge. The opposite or lower end of the module is advanced through an opening in the upper plate until the lower end comes in contact with adaptor (9) within one side of the fluid cartridge. The module then is advanced further until a fluid tight connection between the vial or syringe within the containment module and the adapter in the fluid cartridge is achieved. The provider then mounts the containment module (13) to the cart.

According to step 130, the provider walks the cart from the laboratory where the cartridge was primed to a patient room or other suitable location intended for administering the radioisotope dosage. The location will, of course, depend on the purpose of the radioisotope administration. For treating a condition, the patient may be in a patient room. For a diagnostic procedure, such as a PET scan, the patient may be in a suite with a PET scanner and associated equipment. In either situation, the provider advances the cart to the patient and connects a disposable fluid line from the patient port on the fluid cartridge to an IV line in the patient. The provider then operates the keyboard or screen prompts on the screen to administer the desired volume of radioisotope at the desired flow rate.

At this stage in the process, the pump component in the fluid cartridge is ready to be primed with saline and the radioisotope (step 140). To prime the pump component, the provider first connects a disposable fluid line between a saline syringe mounted on the cart and the saline port of the fluid cartridge. The provider then uses a keyboard or controls on the screen to operate the software to prime the pump. This operation is generally automated and depends at least on the dose to be received by the patient. Further, in step 150 of charging of fluid cartridge with radioisotope the pump draws fluid from the saline syringe and the radioisotope vial (or syringe) into a transfer chamber of the cartridge. At this stage in the process, the pump is primed, charged and the dose is ready to be administered to the patient.

According to step 160, when the radioisotope is being administered, the area of the cart surrounding the screen will be illuminated at a set color indicative of the action being taken. For example, during administration of the radioisotope the illumination may be red, when the administration is almost complete, e.g., 95% complete, the illumination may transition to yellow and when the administration is complete, the illumination may transition to green or blue. The colors are selected to indicate to a viewer of the potential danger from the radioactive isotope. The use of colors in this manner permits a provider operating a PET scanner to view the status of the system from a distance, e.g., the control booth of the PET scanner. If the patient is in a patient room, the provider will be alerted to the danger of radiation while the dose is being administered and know to stay out of the room.

According to step 170, after infusion of the dose some of the radioisotope dose likely remains in the hot dose vessel. To use this residual radioisotope dose, the provider starts a backflush operation to use the residual dose. For this step, the pump withdraws the saline from the saline vessel into the transfer chamber of the cartridge and then pushes that saline into the radioisotope dose vessel. Then after once again the pump loads the radioisotope dose from the radioisotope dose vessel to the transfer chamber to administer the residual dose to the patient. This process is repeated until the entire dose in radioisotope dose vessel is used. The major advantage of this step is that by using a backflushing step waste of radioisotopes dose will be minimized.

According to step 180, when the radioisotope dose is completed, the provider removes the fluid tubing running from the patient IV line to the patient port of the fluid cartridge. The provider then can discard the tubing in the removable container in the cart. The provider similarly can disconnect and place the fluid tubing from the saline syringe in the removable container. The fluid cartridge similarly can be pulled away from the dose transporter and placed in the removable container. The provider then can return the cart to the laboratory for storage and cleaning.

In an embodiment according to the present invention, the theranostic delivery system or radiopharmaceutical drugs delivery system is comprised of a theranostic informatics management system, which consists of a computer screen with graphical user interface (GUI) to receive various patient infusion parameters including one or more of infusion rate, infusion mode, desire dose, desired activity and/or any patient infusion related data. This theranostic informatics system also may include a control system for controlling the infusion process with the status of the light used to show the different states of the device with different colours representing the state of the device.

In an embodiment according to the present invention, the theranostic delivery system or radiopharmaceutical drugs delivery system (100) comprises a contamination management system, which includes a tray with integral channel system to direct any fluid leaks towards a collection pad or waste bin. The theranostic delivery system also includes an accessory management for storage of all infusion supplies including chux, gloves and other equipment.

Another embodiment of the invention in FIG. 6 discloses the front view of the theranostic delivery system or radiopharmaceutical drugs delivery system (100) with a configurable dose transporter (6) that is caddy connected in line with the custom disposable sealed fluid cartridge (7) shielded with viewing window (29) of lead glass. The "Caddy" allows for safe transport of the hot dose between the hot lab and the infusion site.

The theranostic delivery system or radiopharmaceutical drugs delivery system (100) comprises a dose configurable transporter that is a "caddy" which is used to transport the hot dose in a separable radioactive dose transportation and containment module (13) in a syringe of different size from pharmacies to the infusion site. The hot dose in a syringe is shielded in configurable dose shield to protect from radiation emitted from the radiopharmaceutical drug in syringe. Further, the configurable dose transporter (6) is attached with disposable sealed fluid cartridge to start the infusion of drug to patient.

For the infusion of the radiopharmaceutical drugs to the patient comprises four major modes: priming, charging, infusing and backflushing. The priming mode is basically a process of checking for air bubbles or any occlusion in all the infusion lines that are connected with the pump, dose vessel and saline vessel. In the charging mode the disposable fluid cartridge draws the required volumes from the various supply vessel types (saline, hot dose) to an interim volume (i.e., "Transfer") and use that same system in the infusing mode to infuse the patient with the required control of flow rates, accuracy, etc. In the backflushing mode the system is backflushed through the infusion line with specific amounts of saline to the patient to push the residual dose to the patient.

An embodiment of the present invention provides the patient enhanced safety of a radiopharmaceutical drug delivery by ensuring cybersecurity compliance prior to dispensing a radiopharmaceutical drug to the patient. The present process ensures cybersecurity in the radiopharmaceutical drugs delivery system based on the controller being configured to scan the system, network, or connected devices to detect any unauthorized connection and/or malware, prior to infusion of the radiopharmaceutical drug. This configuration and procedure ensures that the system is free from an unauthorized connection and/or malware and alerts the operator about any actual or potential unauthorized connection and/or malware.

In an embodiment of the present invention the controller is configured to force the system into safe mode in case an unauthorized connection or malware is detected. In such an event, the controller is configured to halt operation of the system in case of any threat of an unauthorized connection or malware being detected and maintain that any system operations are stopped until the malware is neutralized.

Each embodiment disclosed herein is contemplated as being applicable to each of the other disclosed embodiments. Thus, all combinations of the various elements described herein are within the scope of the invention.

What is claimed:

1. A radiopharmaceutical drug delivery system comprising;
    a configurable dose transporter;
    a separable radioactive dose transportation and containment module;
    a shielding positioned around at least a portion of the radioactive dose transportation and containment module;
    a disposable sealed fluid cartridge mountable within the configurable dose transporter; and
    a theranostic informatics management system;
    wherein the disposable sealed fluid cartridge comprises:
        a) an adapter to secure a drug vial or syringe to the fluid cartridge;
        b) one or more integrated fluid channels to allow bi-directional flow of fluids;
        c) an integrated precision pump configured to control the flow of a customizable amount of a radioactive drug;
        d) a coded patient port and a coded saline port, wherein the coded patient port and the coded saline port are configured to present differently a patient line and a saline line to a user;
        e) an integral valve system to control flow of fluids through the integrated fluid channels; and
        f) one or more guide features and mechanical interlocks that interact with one or more guide features and mechanical interlocks on the dose transportation and containment module when the fluid cartridge is mounted to the configurable dose transporter.

2. The radiopharmaceutical drug delivery system of claim 1, further comprising a transfer chamber, wherein the disposable fluid cartridge system is insertable into the configurable dose transporter to allow charging of the fluid cartridge with a radioisotope using the pump to draw a fluid from a saline syringe and a radioisotope from the drug vial or syringe into the transfer chamber of the fluid cartridge.

3. The radiopharmaceutical drug delivery system according to claim 1, further comprising one or more pressure sensors to detect a pressure of the patient port and a pressure of saline port.

4. The radiopharmaceutical drug delivery system according to claim 1, wherein the disposable fluid cartridge is configured for withdrawing a customizable volume based on one or more of patient weight, sex, age, health history data and/or other physical parameter.

5. The radiopharmaceutical drug delivery system according to claim 1, wherein the patient port and the saline port are coded to eliminate errors in selection of the patient and the saline lines for connection to the patient port and the saline port, respectively.

6. The radiopharmaceutical drug delivery system according to claim 1, wherein the adapter is tagged with one or more of RFID, barcode or QR code.

7. The radiopharmaceutical drug delivery system according to claim 1, wherein the disposable fluid cartridge comprises a coded port for eliminating errors in connecting a patient line or a saline line to the cartridge.

8. The radiopharmaceutical drug delivery system according to claim 1, wherein the disposable fluid cartridge is configured to be placed in the dose transporter to permit delivery of the radioactive drug via the delivery system.

9. The radiopharmaceutical drug delivery system according to claim 1, wherein the theranostic informatics system comprises a control system for controlling an infusion process with a light used to show different states of the system with different colours representing a state of the system.

10. The radiopharmaceutical drug delivery system according to claim 1, wherein the delivery system further comprises a controller to control an operation of fluid cartridge.

11. The radiopharmaceutical drug delivery system according to claim 1, wherein the configurable dose transporter is configured to be caddy connected in line with the disposable sealed fluid cartridge and to be shielded with a viewing window.

12. The radiopharmaceutical drug delivery system according to claim 1, wherein an infusion of the radioactive drugs to a patient comprises four major modes consisting of priming, charging, infusing and backflushing.

13. The radiopharmaceutical drug delivery system according to claim 12, wherein a priming mode comprises a process of checking for air bubbles or any occlusion in an infusion line that is connected with the pump, dose vessel and saline vessel.

14. The radiopharmaceutical drug delivery system according to claim 12, wherein a charging mode comprises a process of using the disposable fluid cartridge to draw a required volumes of saline and radiopharmaceutical drug to a transfer chamber.

15. A fluid cartridge system for delivering radiopharmaceutical drugs, the fluid cartridge system comprising an enclosure having external walls and an internal volume:
    a) an adapter to secure a vial or syringe containing a radiopharmaceutical drug to the fluid cartridge system;
    b) one or more integrated fluid channels within the enclosure to allow bi-directional flow of fluids;
    c) an integrated precision pump within the enclosure and configured for withdrawing custom amounts of a radioactive drug;
    d) a coded patient port and a coded saline port extending from the enclosure;
    e) a valve system within the enclosure and configured to control flow of fluids in the fluid channels; and
    f) a first sensor and a second sensor;
    wherein, the fluid cartridge system is disposable and is configured to be mounted into a configurable dose transporter to allow an infusion system to withdraw custom amounts of the radioactive drug for infusion to a patient.

16. The fluid cartridge system according to claim 15, wherein the integrated precision pump is shielded to prevent radiation exposure and is configured to protect the patient from an air infusion and comprises an alarm signal for air detection in real-time.

17. The fluid cartridge system according to claim 15, wherein the coded patient port and the coded saline port are configured to prevent errors in selection of patient and saline lines for connection to the patient port and the saline port, respectively.

18. The fluid cartridge system according to claim 15, wherein the fluid cartridge includes an interlock component for interlocking with a dose transporter when the fluid cartridge is mounted in the dose transporter.

19. The fluid cartridge system according to claim 15, wherein the coded patient port is configured to receive a first fluid flow line to deliver a fluid to a patient and the coded saline port is configured to receive a second fluid flow line to receive fluid from a vial or syringe and the first sensor is configured to measure a fluid pressure in proximity to the patient port and the second sensor is configured to measure a fluid pressure in proximity to the saline port.

20. A radiopharmaceutical drug delivery system comprising:
   a configurable dose transporter;
   a separable radioactive dose transportation and containment module;
   a shielding positioned around at least a portion of the radioactive dose transportation and containment module;
   a theranostic informatics management system;
   the fluid cartridge system of claim 15; and
   a controller configured to control an operation of the fluid cartridge system,
   wherein the fluid cartridge system is mounted within the configurable dose transporter, and
   wherein the controller is configured to halt the operation of the drug delivery system in case of any threat of an unauthorized connection or malware being detected and maintain that any operation of the drug delivery system is stopped until the malware is neutralized.

* * * * *